US012802853B2

(12) United States Patent
Koyrakh et al.

(10) Patent No.: US 12,802,853 B2
(45) Date of Patent: Nov. 17, 2026

(54) MODULAR RECONFIGURABLE MAGNETIC NAVIGATION SYSTEM AND METHOD

(71) Applicant: RadWave Technologies Inc., Plymouth, MN (US)

(72) Inventors: Lev Koyrakh, Plymouth, MN (US); Sean Morgan, Golden Valley, MN (US); Andrew Brown, Minneapolis, MN (US)

(73) Assignee: RadWave Technologies Inc., St. Paul, MN (US)

( * ) Notice: Subject to any disclaimer, the term of this patent is extended or adjusted under 35 U.S.C. 154(b) by 579 days.

(21) Appl. No.: 17/278,466

(22) PCT Filed: Sep. 20, 2019

(86) PCT No.: PCT/US2019/052240

§ 371 (c)(1),
(2) Date: Mar. 22, 2021

(87) PCT Pub. No.: WO2020/061504

PCT Pub. Date: Mar. 26, 2020

(65) Prior Publication Data

US 2022/0037085 A1 Feb. 3, 2022

Related U.S. Application Data

(60) Provisional application No. 62/795,737, filed on Jan. 23, 2019, provisional application No. 62/735,049, filed on Sep. 22, 2018.

(51) Int. Cl.
*G01D 5/20* (2006.01)
*H01F 7/08* (2006.01)
(Continued)

(52) U.S. Cl.
CPC ................ *H01F 7/08* (2013.01); *G01D 5/20* (2013.01); *G01D 5/204* (2013.01); *A61B 2034/2051* (2016.02); *H01F 2038/143* (2013.01)

(58) Field of Classification Search
CPC . H01F 38/14; H01F 38/16; H01F 7/08; H01F 2038/143; A61B 2034/2051;
(Continued)

(56) References Cited

U.S. PATENT DOCUMENTS 5,874,881 A 2/1999 Steinbusch
7,764,982 B2 7/2010 Smith et al.
(Continued)

FOREIGN PATENT DOCUMENTS

CA 2815199 A1 11/2014
CN 103557775 A 2/2014
(Continued)

OTHER PUBLICATIONS

5DOF electromagnetic sensor for position and orientation determination, Diagsensor, https://www.diagsensor.com/dst-electromagnetic-sensor/, obtained on Dec. 21, 2024.*
(Continued)

*Primary Examiner* — David M Schindler
(74) *Attorney, Agent, or Firm* — Schwegman Lundberg & Woessner, P.A.

(57) ABSTRACT

A modular electromagnetic navigation system with reconfigurable magnetic field generating antennas provides improved means for tracking various magnetic wired or wireless sensors with multiple biomedical and industrial applications. Electromagnetic field generating antennas (pods) can be implemented as multilayered printed circuit boards (PCB) with different layers being sufficiently aligned and connected in series for increased magnetic field strength.
(Continued)

The pods can be kept separate or implemented on the same PCB as pod assemblies (pads) consisting of spaced apart pods. Different pods and pads can be placed on a side of or around the desired navigation volume allowing creation of arbitrary navigation spaces. Individual pods can also be used as magnetic field sensors or integrated with additional magnetic field sensors allowing localization of the pods in the system to adjust the navigation volume in real time.

11 Claims, 13 Drawing Sheets

(51) Int. Cl.
*A61B 34/20* (2016.01)
*H01F 38/14* (2006.01)

(58) Field of Classification Search
CPC .. A61B 2034/2053; A61B 5/062; G01D 5/20; G01D 5/2006; G01D 5/2013; G01D 5/202; G01D 5/2026; G01D 5/204; G01D 5/2046; G01D 5/2053; G01D 5/206; G01D 5/2066; G01D 5/2073; G01D 5/2086; G01B 7/003; G01B 7/004; H03K 17/945; H03K 17/95; H03K 17/9505; H03K 17/952; H03K 17/9525; H03K 17/953; H03K 17/9532; H03K 17/9535; H03K 17/9537; H03K 17/954; H03K 17/9542; H03K 17/9545; H03K 17/9547; H03L 2017/9527
See application file for complete search history.

(56) References Cited

U.S. PATENT DOCUMENTS 7,835,785 B2 11/2010 Scully et al.
8,648,832 B2 2/2014 Maloof et al.
2001/0045826 A1* 11/2001 Schneider ............ G01D 5/2073 324/207.17
2004/0068178 A1* 4/2004 Govari ................... A61B 34/20 324/207.22
2010/0305427 A1* 12/2010 Huber .................... A61B 34/20 600/424
2011/0080055 A1 4/2011 Dellacona et al.
2011/0224537 A1* 9/2011 Brunner ................. A61B 5/062 600/421
2011/0248846 A1 10/2011 Belov et al.
2013/0015848 A1* 1/2013 Govari ................... A61B 34/20 324/228
2015/0119686 A1* 4/2015 Govari ................... A61B 5/062 600/409
2017/0202627 A1* 7/2017 Sramek .................. A61B 34/20
2020/0237459 A1 7/2020 Racheli et al.

FOREIGN PATENT DOCUMENTS

WO WO-9741985 A1 11/1997
WO WO-2020061504 A1 3/2020

OTHER PUBLICATIONS

"International Application Serial No. PCT/US2019/052240, International Search Report mailed Nov. 20, 2019", 2 pgs.
"International Application Serial No. PCT/US2019/052240, Written Opinion mailed Nov. 20, 2019", 7 pgs.
"Nternational Application Serial No. PCT/US2019/052240, Invitation to Restrict or Pay Additional Fees, and, Where Applicable, Protest Fee mailed Jun. 10, 2020", 3 pgs.
"International Application Serial No. PCT/US2019/052240, International Preliminary Report on Patentability mailed Mar. 31, 2021", 6 pgs.
Bien, Tomasz, et al., "Algorithm for calibration of the electromagnetic tracking system", Proceedings of 2012 IEEE—EMBS International Conference on Biomedical and Health Informatics, [Online]. Retrieved from the Internet: <URL: https://www.researchgate.net/publication/257129292>, (Jan. 2012), 5 pgs.
Jaeger, Herman Alexander, et al., "Anser EMT: the first open-source electromagnetic tracking platform for image-guided interventions", Int J CARS, Springer, (2017), 10 pgs.
O'donoghue, Kilian, "Electromagnetic Tracking and Steering for Catheter Navigation", Doctoral Thesis, National University of Ireland, (Oct. 2014), 290 pgs.
Plotkin, Anton, "New Approaches in Magnetic Tracking", Doctoral Thesis, Ben-Gurion University of the Negev, (Apr. 16, 2009), 134 pgs.

* cited by examiner

MODULAR RECONFIGURABLE MAGNETIC NAVIGATION SYSTEM AND METHOD

RELATED APPLICATION

This application is a U.S. National Stage Filing under 35 U.S.C. 371 from International Application No. PCT/US2019/052240, filed on Sep. 20, 2019, and published as WO 2020/061504 on Mar. 26, 2020, which application claims priority to U.S. Provisional Application Ser. No. 62/735,049 (entitled MODULAR MAGNETIC NAVIGATION SYSTEM, filed Sep. 22, 2018) and to U.S. Provisional Application Ser. No. 62/795,737 (entitled Antenna Pod Matrix, filed Jan. 23, 2019) which are incorporated herein by reference.

BACKGROUND

Many industrial and biomedical applications, including image guided and robotic surgery, have a need for precisely locating instruments and other devices. Localization of various objects including medical devices is often done with the use of the magnetic tracking which requires magnetic field created by some antennas, magnetic field sensors placed on the instruments and other objects and locations, and a data acquisition system capable of processing the data from the sensors and reporting their locations, orientations, etc.

In many practical applications it is desirable that the magnetic field be created for navigating devices within specific volumes, close to the organs of interest or in the volumes that change over the procedure times.

Some instruments and equipment may interfere with magnetic location and sensing methods. Such interference can lead to incorrect location information being displayed, and if used by a surgeon to manipulate medical devices may lead to harm to the patient, so there is a need for detecting such interference.

SUMMARY

Modular and real-time reconfigurable magnetic fields are used to provide tracking of magnetic sensors.

Further provided are a reconfigurable antenna array consisting of individual antenna elements, each creating its own magnetic field with accurate environmentally controlled electrical currents. A plurality of such antenna elements can be used to create magnetic fields in which various magnetic sensor types could be localized, including the antennas themselves when used as sensors. This allows modular deployment of such system depending on the intended use case, reconfiguring the navigation volumes on demand and in real time.

Further, using sensors at fixed locations within the navigation volume and using magnetic field generating antennas as sensors allows an additional level of electromagnetic interference detection and mitigation.

Further, in order to facilitate localization of magnetic field generating antennas for real time reconfigurability, the antennas can be integrated with magnetic sensors.

Rigid structures of magnetic sensors can be embedded around the navigation space in order to facilitate real-time reconfigurability and detect interference.

DETAILED DESCRIPTION

Figure 1:
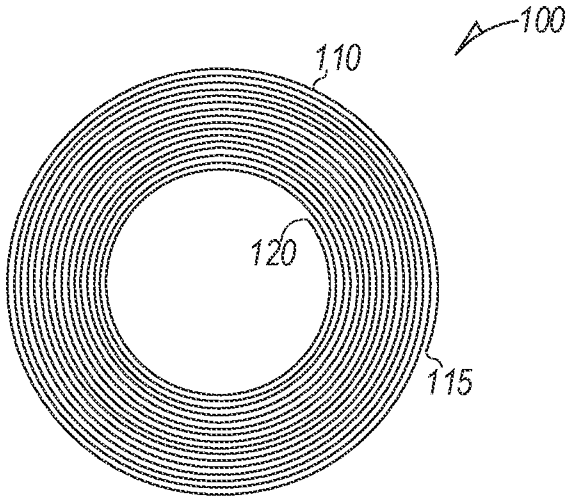
FIG. 1 is a block schematic diagram of a single antenna element referred to as a pod according to an example embodiment.

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

The functions or algorithms described herein may be implemented in software in one embodiment. The software may consist of computer executable instructions stored on computer readable media or computer readable storage device such as one or more non-transitory memories or other type of hardware-based storage devices, either local or networked. Further, such functions correspond to modules, which may be software, hardware, firmware or any combination thereof. Multiple functions may be performed in one or more modules as desired, and the embodiments described are merely examples. The software may be executed on a digital signal processor, ASIC, microprocessor, or other type of processor operating on a computer system, such as a personal computer, server or other computer system, turning such computer system into a specifically programmed machine.

The functionality can be configured to perform an operation using, for instance, software, hardware, firmware, or the like. For example, the phrase "configured to" can refer to a logic circuit structure of a hardware element that is to implement the associated functionality. The phrase "configured to" can also refer to a logic circuit structure of a hardware element that is to implement the coding design of associated functionality of firmware or software. The term "module" refers to a structural element that can be implemented using any suitable hardware (e.g., a processor, among others), software (e.g., an application, among others), firmware, or any combination of hardware, software, and firmware. The term, "logic" encompasses any functionality for performing a task. For instance, each operation illustrated in the flowcharts corresponds to logic for performing that operation. An operation can be performed using, software, hardware, firmware, or the like. The terms, "component," "system." and the like may refer to computer-related entities, hardware, and software in execution, firmware, or combination thereof. A component may be a process running on a processor, an object, an executable, a program, a function, a subroutine, a computer, or a combination of software and hardware. The term, "processor," may refer to a hardware component, such as a processing unit of a computer system.

Furthermore, the claimed subject matter may be implemented as a method, apparatus, or article of manufacture using standard programming and engineering techniques to produce software, firmware, hardware, or any combination thereof to control a computing device to implement the disclosed subject matter. The term, "article of manufacture," as used herein is intended to encompass a computer program accessible from any computer-readable storage device or media. Computer-readable storage media can include, but are not limited to, magnetic storage devices, e.g., hard disk, floppy disk, magnetic strips, optical disk, compact disk (CD), digital versatile disk (DVD), smart cards, flash memory devices, among others. In contrast, computer-readable media, i.e., not storage media, may additionally include communication media such as transmission media for wireless signals and the like.

Various medical interventions including surgery have a need for precisely locating/tracking instruments and other devices. Some instruments may interfere with magnetic location and sensing methods. Such interference can lead to incorrect location information being displayed for use by a surgeon to manipulate devices, leading to harm to the patient.

The magnetic navigation system can track the locations of magnetic sensors embedded in medical instruments and other objects by utilizing multiple reconfigurable antennas. Applications of the system include but are not limited to medical and industrial.

The magnetic navigation system described in this invention is reconfigurable and adaptable for different applications. Simple mapping with real-time self-calibration capabilities can be utilized.

Applications of the navigation system include tracking biomedical instruments within the human body. Antennas may be implemented as printed circuit boards (PCBs) and can be placed close to the organs of interest, including being attached to the human body using suitable adhesives. Such antennas may be placed on the patient's body, including around the patient's torso for thoracis and lung surgeries, head in order to track intracranial tools, etc.

Antennas of various shapes and sizes can be created for any special case and used with a standard piece of hardware.

Principles of operation include at least some of the following:

Antenna coils can be formed as printed circuits or attached to different layers that are coupled together. Multiple layer PCBs (printed circuit boards) can be used with specifically chosen shapes of traces on individual layers in order to increase the magnetic field strength and/or shape the magnetic field in a desirable way. Such PCBs may be referred to as individual antennas "pods" or "elements".

Each antenna pod is capable of emitting and/or sensing electromagnetic fields. Pods can be arranged in different planar or 3D configuration for the desired navigation scenario. The pods can be placed into a predesigned matrix, thus providing highly predictable magnetic field configuration. The field configuration will be defined by the known geometry of the matrix.

The system can be used for localization and tracking sensors or emitters. Emitters are coils emitting magnetic fields. While the system is operational without magnetic field mapping, mapping, if desired, can be performed in short time by using a fixture containing multiple sensors placed at a single or several locations.

A sensor or a sensor assembly is localized by finding a location within the localization volume at which the antennas produce magnetic fields, which generate responses matching those sensed by the sensor or the sensor assembly. At a given location in the navigation volume each antenna generates a magnetic vector field B(i, x, y, z), where i is the antenna number which creates the field. This magnetic field is being sensed by the local sensor (or sensor assembly) located at the point (x,y,z) which outputs the voltage values corresponding to the magnetic field strength B(i, x, y, z) and the sensor orientation vector (or set of vectors for sensor assemblies) m(j), where j is the sensor coil number in the sensor assembly.

The pickup voltages are determined for each sensor by the equation V(i, x, y, z)=f(m, B(i, x, y, z)), where function B(i, x, y, z) depends on the exact antenna shape and construction and can be computed from the known antenna geometry using the Maxwell equations or measured at the antenna manufacturing or installation time. The function f(m, B(i, x, y, z)) is determined based on a specific signal processing approach chosen for the system and can be implemented in hardware, software or a combination thereof. For each location and orientation of the sensor in the magnetic field of the given antennas configuration these equations form a system which can be solved by using one of the known numerical methods for solving nonlinear equations.

One such widely used method is based on the minimization of the error between actual sensor pickups and the pickups expected for a sensor at a chosen location and orientation. Specifically. Levenberg-Marquardt minimization method can be used for solving the above system of equations.

Various antenna shapes and configurations will result in different sets of functions B(i, x, y, z) which describe the magnetic field in which the sensors are localized. These functions can be computed based on the Maxwell equations, or measured at the antenna manufacturing time. The process of measuring the antenna's magnetic field within the navigation volume is called mapping.

Also, different combinations of sensors can be used locally to provide solutions for the desired number of degrees of freedom. Such combinations of sensors can affect the requirements on the geometry and number of the antenna elements. The number of antennas, and therefore the number of distinct magnetic fields, must be sufficient for the localization of a specific sensor type. For example, it is known from the basic electrodynamics theory that a sensor formed by a combination of three non-coplanar coils would require a minimum of three such magnetic fields, while a single coil magnetic sensor with a known coil characteristic would requires at least five distinct antenna fields for unambiguous localization. In practice, however, a single coil sensor localization often requires significantly more than five geometrically distinct antenna fields due to the properties of the mathematical equations involved.

The proposed navigation system design can be used for tracking sensors of different types by providing the necessary number of antennas for each implementation.

In a configuration when antennas are used to generate magnetic fields, they can be used with magnetic sensors in catheters or other medical or non-medical devices and the information from those sensors can be used for the device localization and tracking.

In this case multiple strategies can be employed in order to separate sensing inputs from different antennas; such as time or frequency division-multiplexing and other strategies.

Magnetic field generating antennas can also be used for sensing magnetic fields.

In a configuration when the antennas are used for sensing the magnetic field, such magnetic field can be emitted from the emitter located in the medical device or a pill within and/or outside the patient's body. In this case inputs from different antennas can be processed for determining the location and orientation information of the emitters. For multiple emitters different frequencies and or pulses separated by time can be used in order to determine which signal belongs to which emitter. Triangulation or trilateration may be used for determining locations of emitters.

Stationary pods-antennas can be combined with the ones residing on patches placed on the patient, when used with a real-time self-calibration/mapping algorithm.

Wireless emitters and sensors can be used with these antennas.

A specific algorithm allowing wireless sensing suitable for accurate localization may be based on triangulation, trilateration, or combinations thereof.

The signals from the emitters or/and antennas are sent to a computer through wired or wireless connections and are processed to extract the location information.

In addition to location, different autonomous devices can also transmit other information, which can also be received by the antennas described herein.

Magnetic sensors and/or emitters and electrical circuits for wireless signal processing and communication with outside antennas can be built within small pill-sized form factors for various medical or non-medical applications.

For the purposes of tracking, pill-sized devices within the human body, the antennas may be made as flexible patches that can be attached to the patient for the required periods of time. Such antennas can be collecting information from the device or communicating commands to the device in addition to the localization of the device.

The power supply for such antennas can be made portable and attached to or worn by the patient as well.

The antennas can be controlled by devices also attached to or worn by the patients. Examples of such devices are various micro-computers including but not limited to phones.

Depending on the particular use case, a wide range of wired and wireless connectivity options can be deployed with such antennas, including Wi-Fi, cellular and so on.

FIG. 1 is a block schematic diagram of a single antenna element referred to as a pod 100 according to an example embodiment. One level of antenna pod 100 is shown as a conductor 110 formed in a spiral shape to optimize a number of turns that can be achieved. A first end 115 of the spiral shape may be used as a first contact with a second end 120 used as a second contact. While shown as a circular spiral, other shapes may be used, such as a square, triangle or other polygon or curved shape, or combination thereof depending on manufacturability. Common photolithographic techniques may be used to form the pod.

The single antenna pod 100 can consist of multiple layers of antenna elements on a PCB. Different layers can be connected in series or parallel in order to adjust the magnetic field strength, field geometries etc. The number of layers can be optimized based on the magnetic field strength requirements, compatibility with other equipment and manufacturing costs, etc. Multiple layers would normally only require less than 5 mm of total PCB thickness. The layers may be laminated together, or additional layers may be attached or grown with conductor material comprising the antenna elements deposited on attached or grown layers. Conductive vias or through holes and conductive traces or other means of serially connecting the multiple antenna elements on different layers may be used between the first and second ends 115 and 120 of antenna elements on the different layers such that current flows through the antenna elements in a same direction, additively contributing to the magnetic field generated or sensed. For example, between a first layer antenna element and a second layer antenna element, the first end 115 of the first layer antenna element may be coupled to a driver or sensing device, such as a controller. The second end 120 of the first layer antenna element may be coupled to the first end of the second layer antenna element, and the second end of the second layer antenna element may be coupled to either a third layer antenna element, or the driver/sensing device. Several layers may be coupled in the same manner to form a multilayer antenna pod, represented by antenna pod 100.

Figure 2:
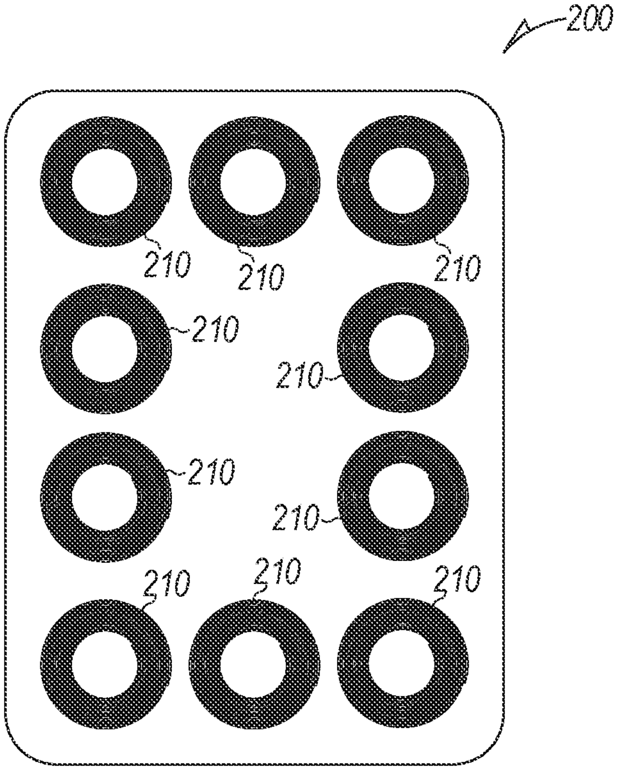
FIG. 2 is a block schematic diagram of a configurable arrangement of pods on an antenna matrix representing a pad according to an example embodiment.

FIG. 2 is a block schematic diagram of a configurable arrangement of pods on an antenna matrix (pad) 200. The assembled pads can have small thickness, e.g. of less than 10 mm including mechanical enclosures, and fitted on virtually any surgical table. In one embodiment, the spirals of the antenna elements comprise equal distant circular lines of decreasing radius. Ten pods 210 are illustrated in pad 200 and shown arranged in a rectangular shape with the pods defining a perimeter. Other numbers of pods and shapes may be used in further embodiments.

Pods may be connected to a controller to individually actuate the pods. In one example, one pod may be driven with current to create a magnetic field, and the other pods may generate current in response to the magnetic field, acting as sensors. In effect, the pad may operate as a transceiver, with one or more pods transmitting and one or more other pods receiving by measuring responses.

Figure 3:
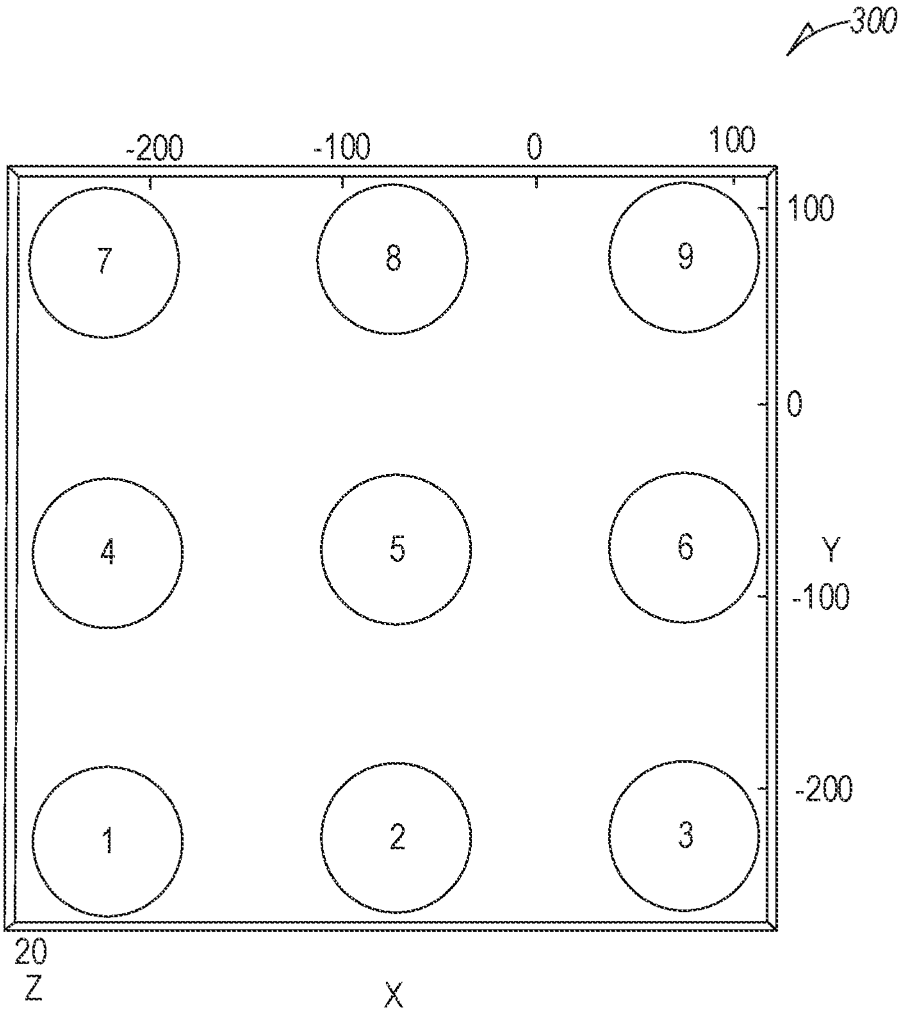
FIGS. 3 and 4 illustrate pads and having different arrangements of pods on the pads according to an example embodiment.
Figure 4:
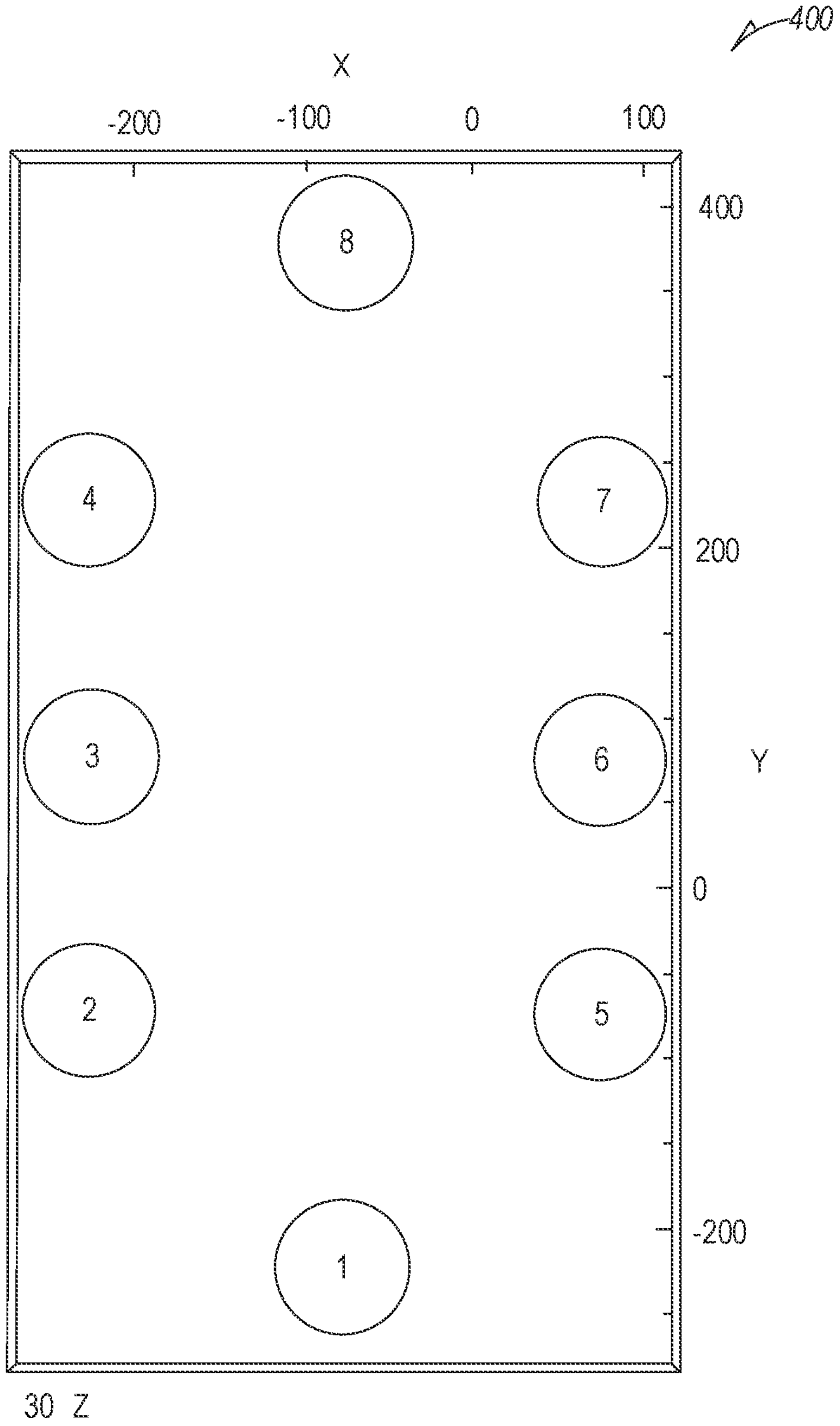

FIGS. 3 and 4 illustrate pads 300 and 400 having different arrangements of pods on the pads. The pods may be single or multiple antenna element pods, which may vary in the number of levels in each pod, and the number of turns in a spiral or other shape of antenna element. In order to accurately track sensors, antennas often require magnetic field mapping, which involves measuring magnetic fields created by the antenna at multiple locations in the navigation volume.

Antenna pods and elements made as traces on printed circuit boards lend themselves to computation of magnetic fields with very high precision such that mapping may not be needed for the individual antenna elements or pods. However, for antennas consisting of multiple antenna elements it is important to know where the elements are located in respect to each other. A limited number of measurements made at known locations with magnetic field sensors can be used to determine such locations. This procedure is also called mapping. In this case, the antenna elements are localized in respect to the known locations of the magnetic field sensors.

Antenna elements, can in turn, be also used for mapping locations of other antenna elements.

In one embodiment, real-time self-mapping of the antenna pods may be performed. Various antenna configurations allow mapping/calibration of the antennas.

Figure 5:
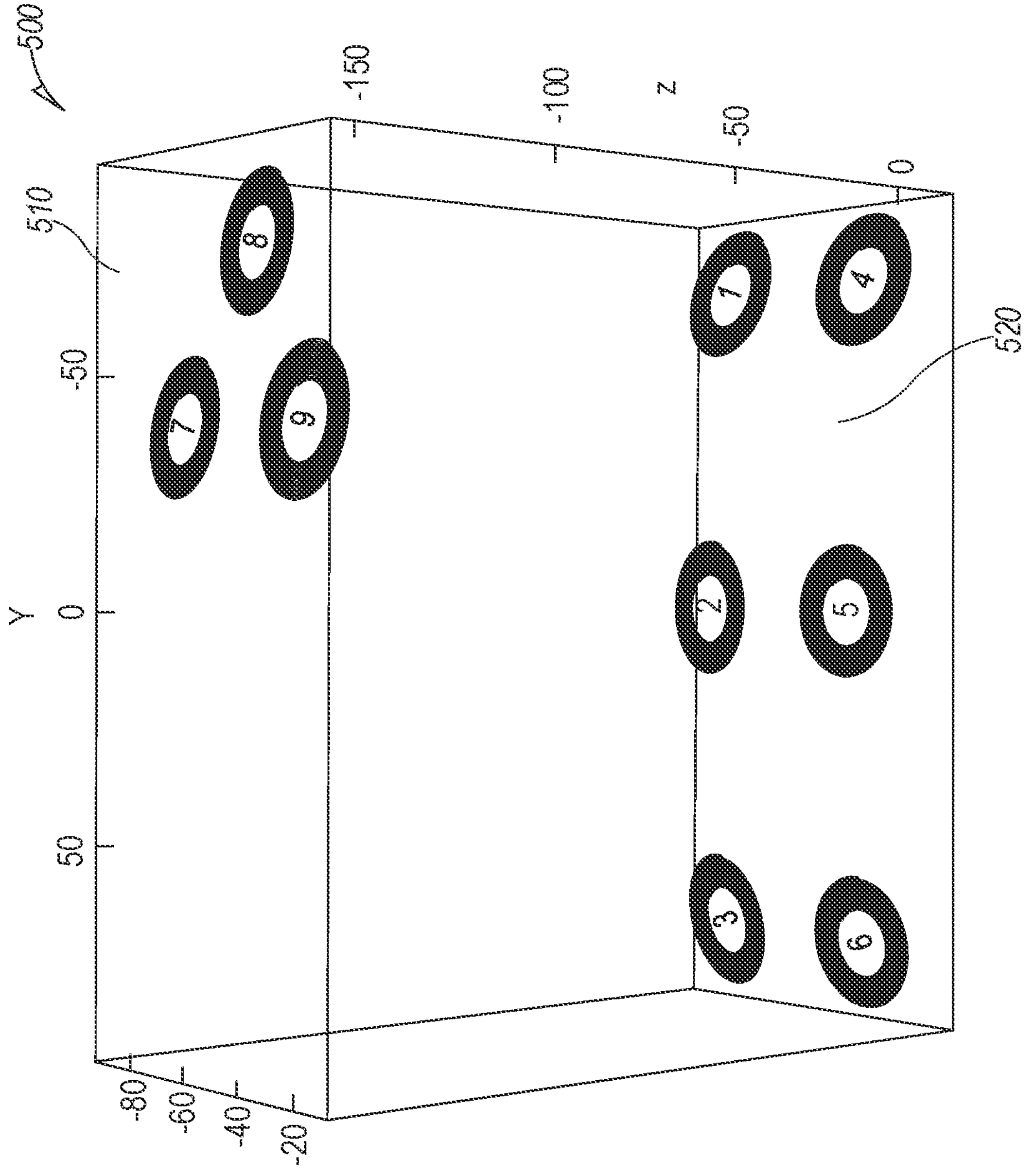
FIG. 5 is a block schematic diagram illustrating a pod configuration for use in real-time self-mapping of antenna pods according to an example embodiment.

FIG. 5 is a block schematic diagram illustrating a pod configuration 500 for use in real-time self-mapping of antenna pods.

One patch/pad 510 with antenna pods is placed on the back of the patient. Another patch/pad 520 with antenna pods is placed on the chest of the patient. Self-mapping consists of exciting antennas or pods one-by-one and measuring responses detected by other antennas.

Another real-time self-mapping technique can be accomplished with dedicated electromagnetic field emitters at known locations/orientations in respect to each other.

In one embodiment, self-mapping may be performed by exciting antennas/pods one-by-one and the responses are recorded on other antennas. The responses are then processed in order to reconstruct relative locations and orientations of the antennas. This technique requires some of the antennas to be fixed in respect to each other, while other antennas can change their relative locations and orientations with time.

Once locations and orientations of the antennas are known, the navigable emitters or sensors can be localized within the navigation volume.

Navigable sensors/emitters are not shown.

In pod configuration 500, three antennas in pad 510 are assumed to be mounted on a rigid substrate, while the bottom antennas in pad 520 can be placed on a fully flexible substrate. The rigid substrate-based antennas of pad 510 can be placed on the patient's stem, while the flexible substrate-based antennas of pad 520 can be placed on the back of the patient.

The decision on which antennas go to which part of the patient may depend on the procedure and various other factors. The self-mapping procedure may be computationally and numerically stable.

Figure 6:
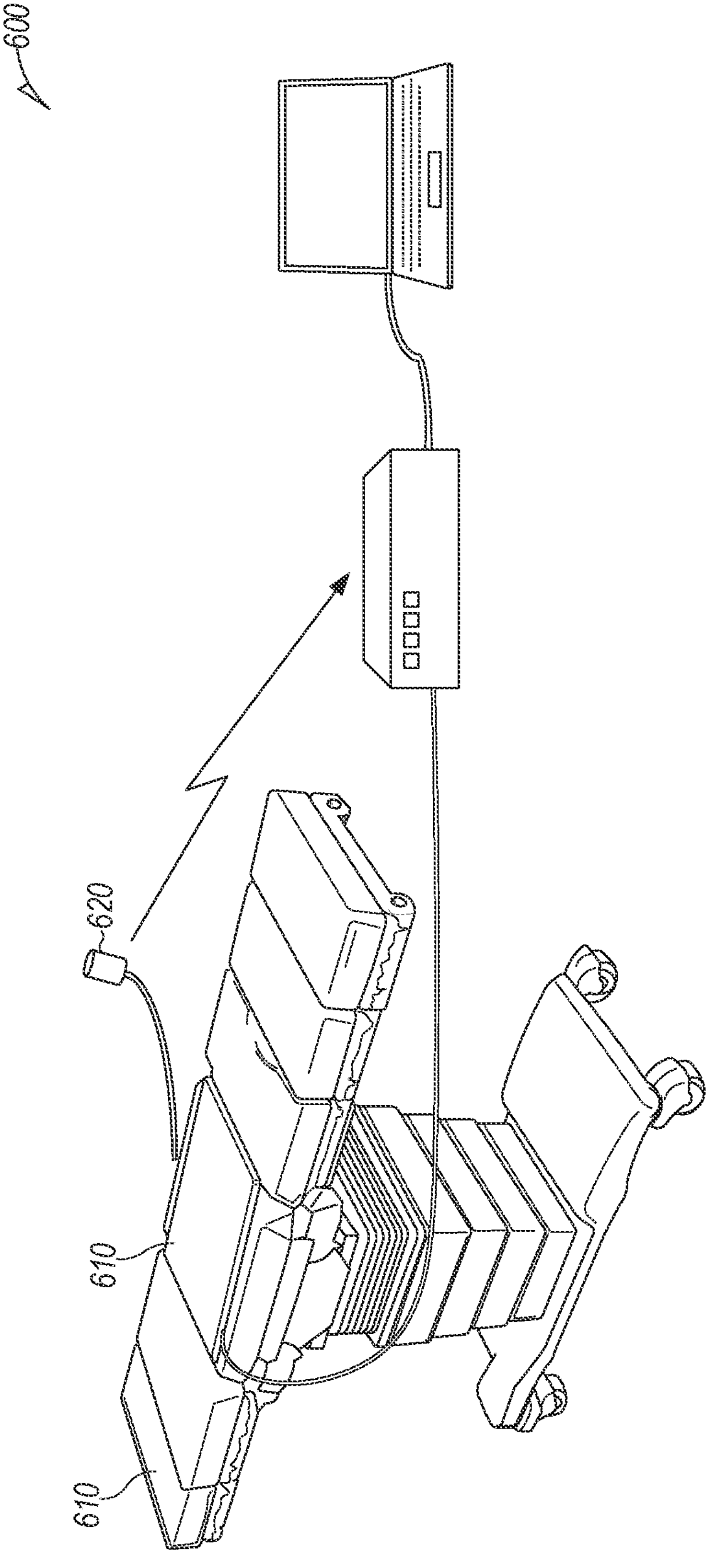
FIG. 6 is a perspective view of an operating theater having an examination or operating table shown with a rectangular pad having pods on the table according to an example embodiment.

FIG. 6 is a perspective view of an operating theater 600 having an examination or operating table 610 shown with a rectangular pad 610 having pods on the table 610. A tool, in this example, a catheter 620 with one or more pods or sensors, such as a wireless sensor, is shown for communicating with a local base station that is linked to a computer running an application. Wires are also illustrated as connecting to the pad or multiple pads having pods with different configurations or content. Individual pods are activatable in various embodiments.

In some embodiments, the pads are expandable and adaptable. In order to cover a greater navigation volume, multiple patches containing antennas can be used (e.g. placed on different parts of the patient's skin) and made to work together through self-calibration.

Some of the many uses for the pads and pods are now described.

Pods comprising single or multilayer PCBs used as antenna building blocks. Modular magnetic field antennas can be assembled from the pods. The modular assembled antennas can be either fixed or placed on fixtures/patches around the navigation volume.

A special mapping procedure would either not be required or mapping can be accomplished in a short time using a mapping fixture consisting of several sensors such as the pod configuration 500 shown in FIG. 5, which can be connected in sequence or simultaneously to mapping hardware and software.

The sensors on the mapping fixture allow precise determination of locations and orientations of all antenna pods in very short time. The locations and orientations of the pods provide sufficient information for accurate navigation of sensors. Various algorithms for self-calibration of the navigation system to maintain accuracy during navigation can be applied.

Multiple wired or wireless sensors can be tracked. Wireless sensor use may be based on demodulation algorithms that are similar to the wired sensors, with raw or demodulated pickups communicated to the equipment computing locations via a wireless link. A synchronizing protocol may be used to keep magnetic fields' waveforms and raw waveforms picked up by the wireless sensors synchronous.

An algorithm allowing wireless sensing suitable for accurate localization may be used. The navigation system is very scalable in terms of the number of antennas and sensors used for any practical application. The system can be positioned close to the areas of interest or spread over greater areas and volumes. The system can automatically switch to the areas of interest as the localization targets move by actuating different pods or sets of pods, also providing the ability to track multiple targets simultaneously.

Many existing navigation systems on the market cannot work on large people or objects. On the other hand, the existing system's magnetic field antennas' sizes are often limited by the hospital bed sizes and other logistic considerations. Pads may be formed as patches for applying directly to people. In this situation a patches-based system which can be placed on any patient in the way to ensure navigation in any particular region can aide the overall procedure. The patches can also be used with existing systems and different external antennas in order to improve localization in specific areas where the original system's magnetic field-based localization fails. They can be also added interprocedurally if need arises.

Figure 7A:
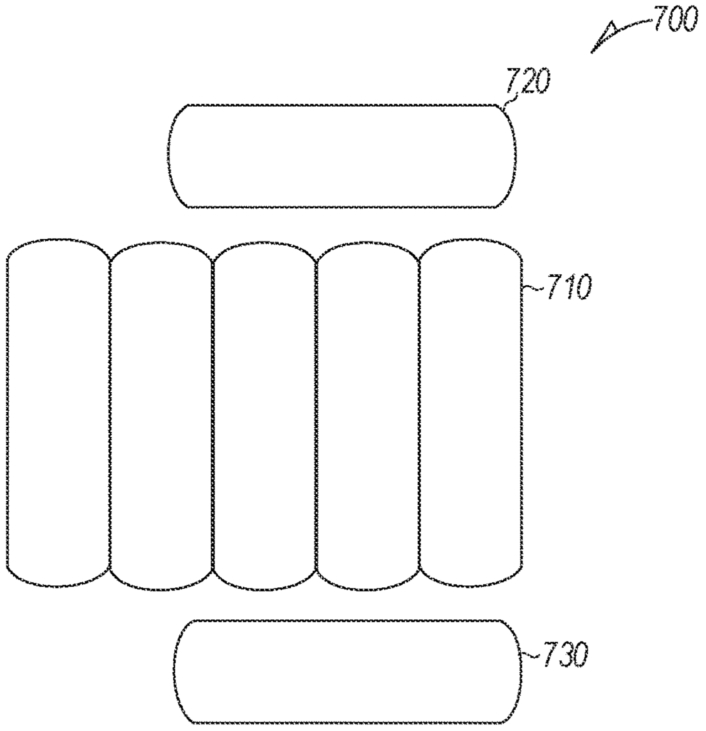
FIG. 7A is block diagram illustrating the use of pods and pads for configurable navigation spaces according to an example embodiment.

FIG. 7A is block diagram illustrating the use of pods and pads for configurable navigation spaces generally at 700. Multiple sections are shown in one such configuration that includes a set of adjacent pads 710 along with two opposing pads 720 and 730 arranged at opposing sides of the adjacent pads 710

Each section may be in the form of one or more pads that may contain multiple antenna pods. The sections, pads, and/or pods can be switched on/off independently. Sections can be positioned at different places and spatial orientations, as the configuration 700 is just one example.

One or more sections can be connected to the same antenna pod driver circuitry. Navigation space is the volume around magnetic field generating antennas where a sensor can be localized. Dynamic navigation spaces may be created by the use of the sections, and the sections can be reconfigured prior or during a procedure.

The configurable navigation spaces can be useful in situations where instruments carrying sensors need to be localized in places potentially relatively far from each other, so that a fixed magnetic field generator setup is insufficient.

The antenna pods and their assemblies (sections) can be arranged in arrays, which can be switched on and off for use for localization of 5DOF (degrees of freedom) and/or 6DOF magnetic sensors.

Additional antenna sections can be brought or removed and/or switched on and off in real time. The navigation domain can be continuously created, changed and adjusted in real-time for localization needs.

Antenna pods can be connected serially or in parallel generating the same magnetic field frequencies. This will aid in modifying the effective field pattern for a given magnetic field component/frequency. Also, this method can be used to increase spatial field gradients, which can aid in producing more robust solutions to the localization problem.

Antenna pods can be used as field generators and/or they can be used as field sensors to measure fields from other antennas or smaller field generating devices in the navigation volume.

The magnetic fields from the antenna pods can be mapped in real time using other pods as sensors or specialized sensors embedded into surrounding space, including within the antenna pods themselves or their housing.

Figure 7B:
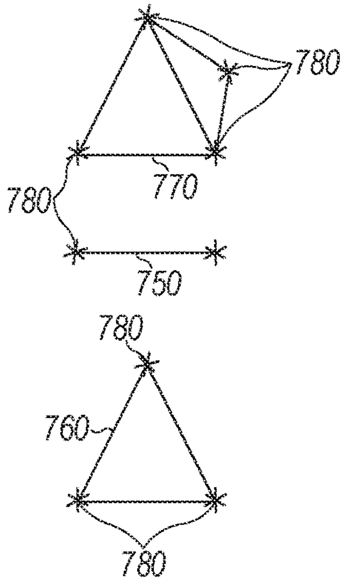
FIG. 7B illustrates three different example rigid structures supporting multiple sensors that serve as real-time field mapping devices according to an example embodiment.

FIG. 7B illustrates three different example rigid structures 750, 760, and 770 supporting multiple sensors 780 that serve as real-time field mapping devices. They may be referred to as rigid sensor assemblies.

5DOF or/and 6DOF sensors 780 are placed at the vertices of a rigid structure, such as a stick 800, triangle 760 or a tetrahedron 770. Other two dimensional and three-dimensional rigid structures may be used in further embodiments. The distances between the sensors are known to a very high precision. Such structure can be made with materials which do not distort magnetic fields, such as plastic.

Using the magnetic field-based location measurements, the "measured" distances between sensors and their orientations are computed. The distances and orientations are monitored in real-time. Any observed changes in the distances and orientations can be interpreted as disturbances of the navigation electromagnetic field caused by external sources.

For a different application, the rigid sensors assemblies can be freely moved in the magnetic fields within the navigation volume of interest and the reconstructed locations/orientations of the sensors can be recorded.

Then, by applying differential geometry equations, the 3D navigation space can be accurately reconstructed so that measured 3D locations and orientations of other magnetic sensors could be accurately mapped into the 3D navigation space.

These sensor assemblies can be used both for measuring magnetic field maps, and for continuous monitoring and compensating of the magnetic field distortions due to environmental factors such as the presence of the external metal.

Figure 8:
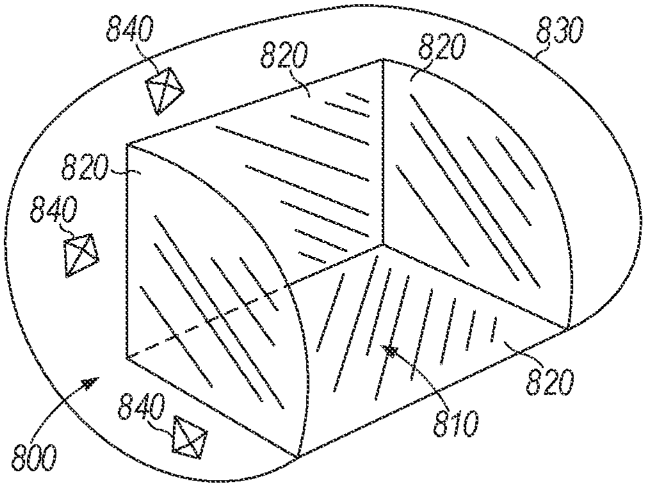
FIG. 8 is a block perspective view of an example EM tracking volume 800 enclosed within the surfaces containing the pads with antenna pods according to an example embodiment.

FIG. 8 is a block perspective view of an example EM-tracking volume enclosed within the walls containing the pads with antenna pods 800 according to an example embodiment. A navigation space 810 may be created by combining antenna pods built into the walls 820 of the desired navigation volume. The volume 800 may be supported by an enclosure 830. 5DOF and/or 6DOF magnetic sensors 840 are localized within the space. The enclosure 830 can be shielded using various magnetically insulating materials to guard from external magnetic field interferences.

Figure 9A:
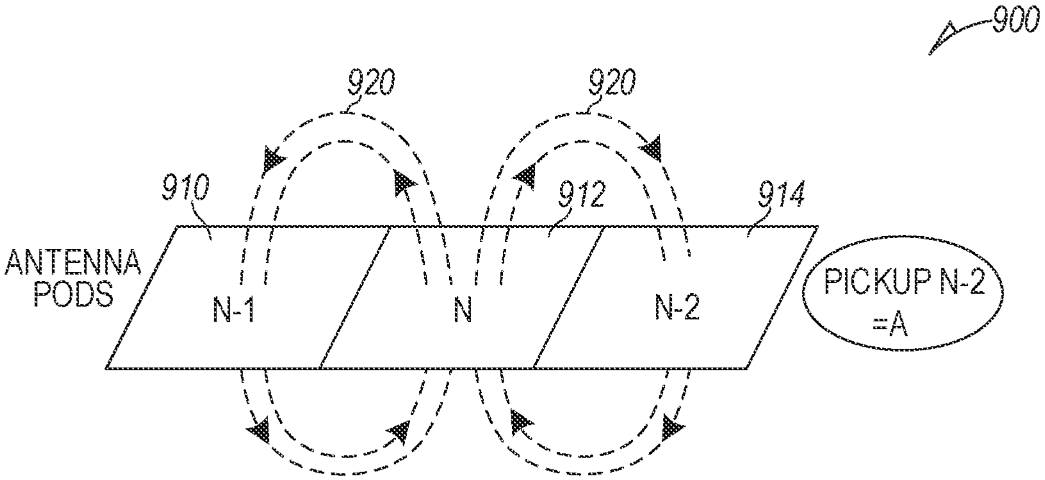
FIG. 9A is a schematic representation of a real-time interference detection system according to an example embodiment.

FIG. 9A is a schematic representation of a real-time interference detection system 900. For a system with N antenna pods, each antenna can monitor the fields from the N−1 other antenna pods. An array of three antenna pods (N−1, N and N−2). The center antenna pod (N) is generating a magnetic field and the field is sensed by the other two antenna pods (N−1 and N−2).

Figure 9B:
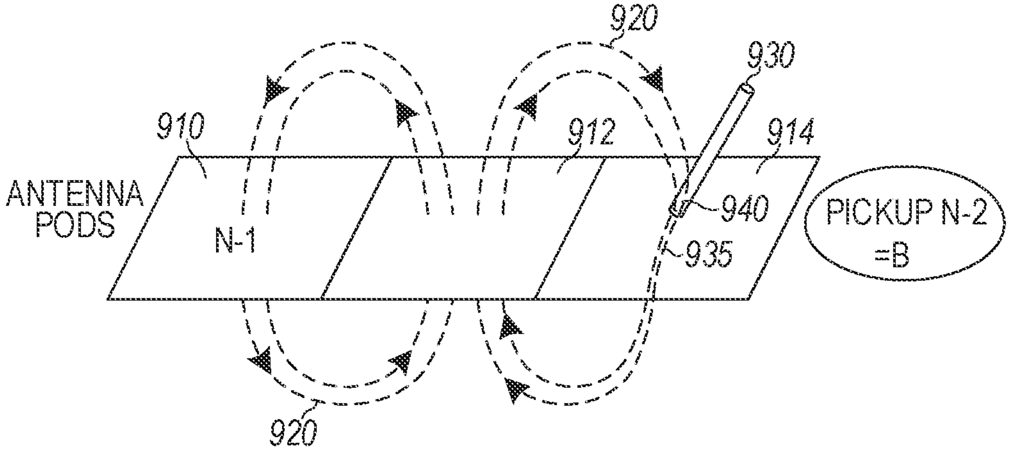
FIG. 9B is a schematic representation of a real-time interference detection system including an interfering object according to an example embodiment.

Three adjacent sets of antenna pods 910, 912, and 914 are illustrated with lines of magnetic flux indicated as broken lines 920. The pods are labeled N−1, N. and N−2 respectively. The magnetic field measured by pod 914 is designated as pickup N−2 and is illustrated as picking up signals having a value of A. FIG. 9B is the same schematic representation with consistent reference numbers with the addition of an object 930 illustrated near pods 914. Note that the lines of flux near the object 930 are disturbed as illustrated at 935 and 940. This disturbance is picked up as a change in the magnetic field sensed by pod 914 and has a value of B, which is not equal to A, signaling that interference has been detected at pod 914, which may be a single antenna or antenna element.

Figures 10A, 10B:
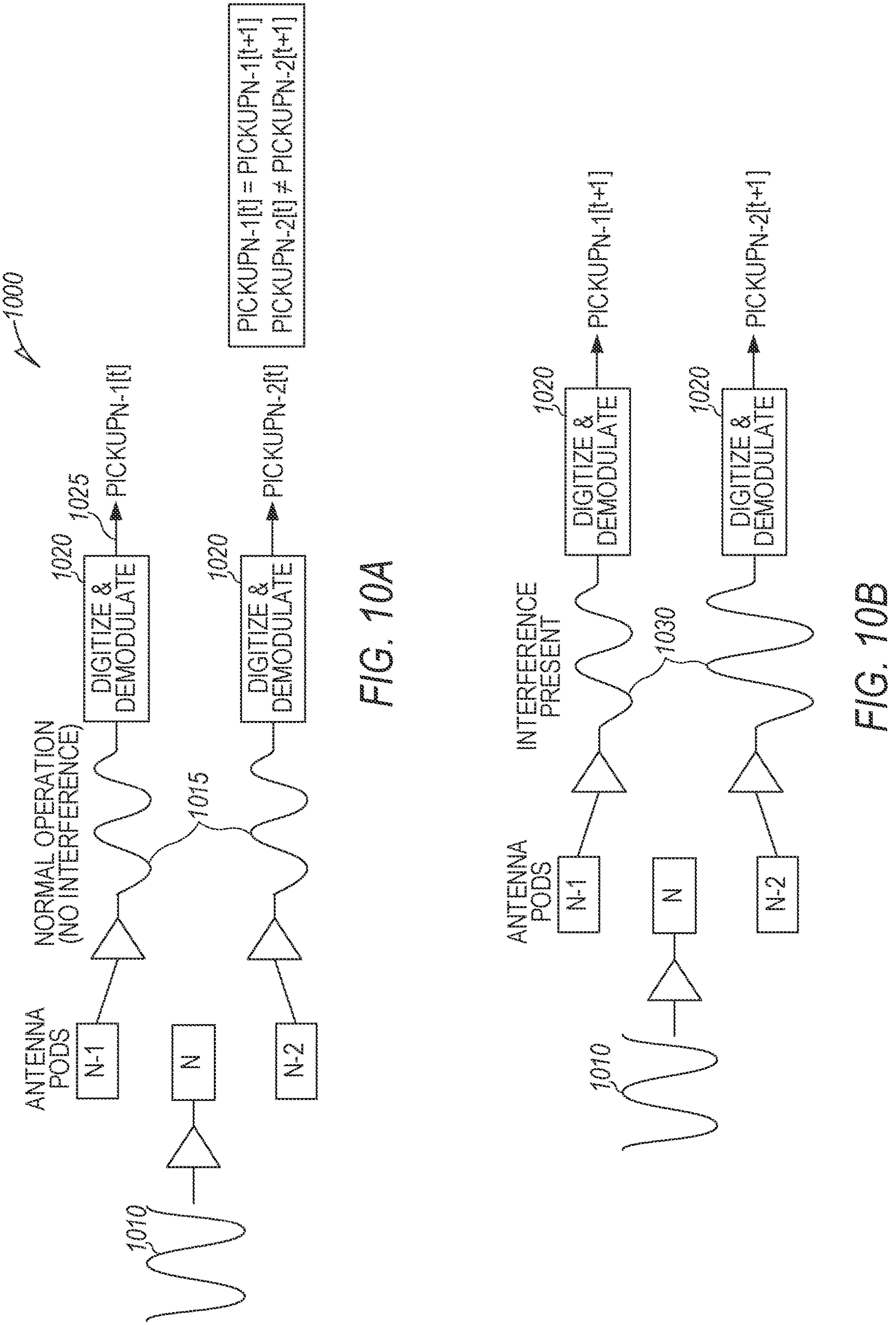
FIG. 10A is a schematic block diagram illustration of normal operation of the interference detection system according to an example embodiment.
FIG. 10B is a schematic block diagram illustration of interference in the interference detection system according to an example embodiment.

FIG. 10A is a schematic block diagram illustration of normal operation of the interference detection system 900 indicated generally at 1000. Antenna pods will primarily be used to generate magnetic fields within the navigation volume, but they can also be used to simultaneously monitor fields from the other antenna pods in the system. Signals 1010 are shown driving antenna pod N. Signals 1015 are sensed by antenna N−1 and N−2 are illustrated as a response to the field generated by antenna N. These waveforms can be digitized and demodulated by circuitry 1020 into a pickup proportional to the amplitude of the sensed waveform (pickup value A in FIG. 9A). This pickup can be measured for normal conditions where no interference is present.

FIG. 10B illustrates system 900 having reference numbers consistent with FIG. 10A for the case where interference is present due to a foreign object (ex. bed arm, some magnetic material, or some other metallic material) being brought into the sensing volume resulting in the field generated by antenna N being distorted. Due to the interference, the signal 1030 sensed by antenna N−2 as a response to the field generated by antenna N is different, as the field has been distorted. The signal 1030 sensed by antenna N−1 as a response to the field generated by antenna N is unchanged. In this example, the field sensed by antenna N−2 has a larger amplitude than before and therefore produces a different pickup (pickup value B in FIG. 9B) than the pickup produced in normal operation (pickup value A in FIG. 9A).

This difference in pickups A and B may be used as an additional interference detection method as well as a warning mechanism for users. Also, in combination with the known theoretical magnetic field pattern that would be produced by antenna pod N or any other antenna pods, the magnetic field map may be adjusted to aid in compensating for these disturbance affects.

Figure 11A:
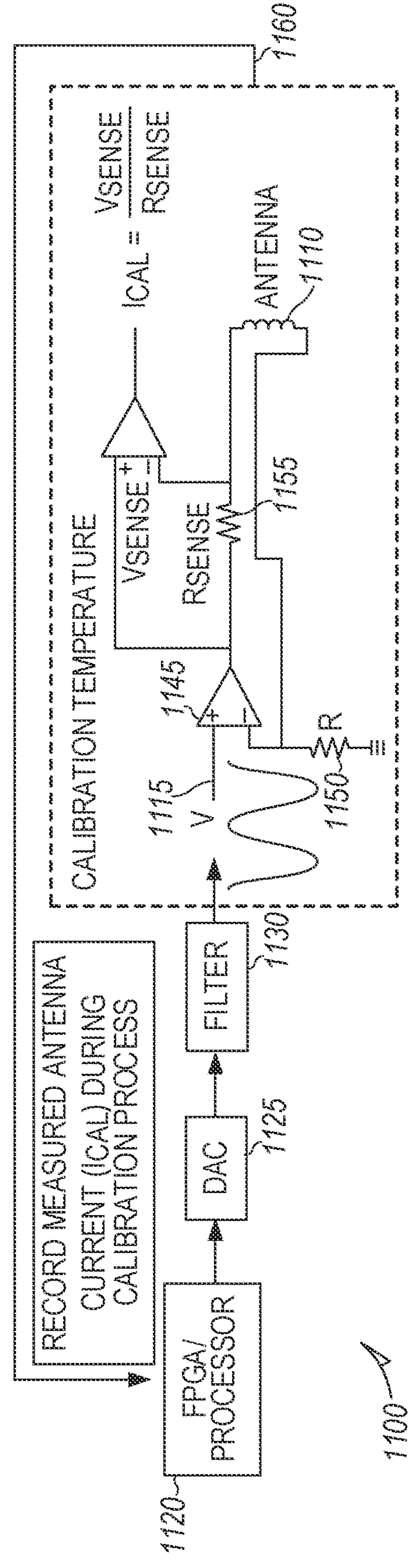
FIG. 11A is a block schematic diagram of a voltage controlled constant current circuit during calibration according to an example embodiment.

FIG. 11A is a block schematic diagram of a voltage controlled constant current circuit 1100 for maintaining accurate current amplitudes in the antenna elements in the presence of external influences such as varying environmental temperatures. Circuit 1100 comprises a voltage controlled constant current used to drive AC current through the antenna pod 1110 with the goal of generating known magnetic fields that can be sensed by magnetic sensors and/or other antenna pods in the navigation volume. A pad that includes one or more pods may include circuitry and a power source, such as a battery coupled to drive pods to create magnetic fields and/or receive current from pods subjected to magnetic fields. The circuitry may digitize the current and act as a transceiver to wirelessly transmit and/or receive data, creating a wireless magnetic sensor.

A voltage control 1115 (V), which is often a sinusoidal waveform, is synthesized by an FPGA or processor 1120 along with a Digital to Analog Converter (DAC) 1125. There may also be various low pass and/or high pass filter stages 1130 between the DAC 1125 and the non-inverting input of a power amplifier 1145 to produce a higher fidelity input waveform.

The filtered DAC output 1150 is coupled to a non-inverting input of the power amplifier 1145. In an effort to minimize the difference between the non-inverting and inverting inputs, the power amplifier 1145 drives the current required to produce V across a high-power low impedance resistance R 1150 connected to the inverting input of the power amplifier 1145.

One shortcoming of the voltage controlled current feedback circuit 1100 is the environmental variability in circuit components such as the high power low impedance resistor (R) 1150, the power amplifier 1145, and/or the filter components 1130 between the DAC 1125 and the non-inverting input of the power amplifier 1145.

To mitigate this, the circuit 1100 can be calibrated at room temperature while measuring the current through a high precision, low resistance, low environmental variability resistor ($R_{sense}$) 1155 producing the differential voltage ($V_{sense}$) 1160. This calibration current ($I_{cal}=V_{sense}/R_{sense}$) is recorded in non-volatile memory of processor 1120 for later use.

When environmental conditions different from the calibration conditions are experienced during normal operation, component variations may occur. For example, the resistance of R 1150 changes by some number (~50 to 200) of parts per million per ° C., which would cause a change in the amplitude of the current through the antenna pod 1110. Using $R_{sense}$ 1155, the antenna pod current (I) is continuously monitored and compared to the calibration current ($I_{cal}$) within the processor or FPGA 1120.

Figure 11B:
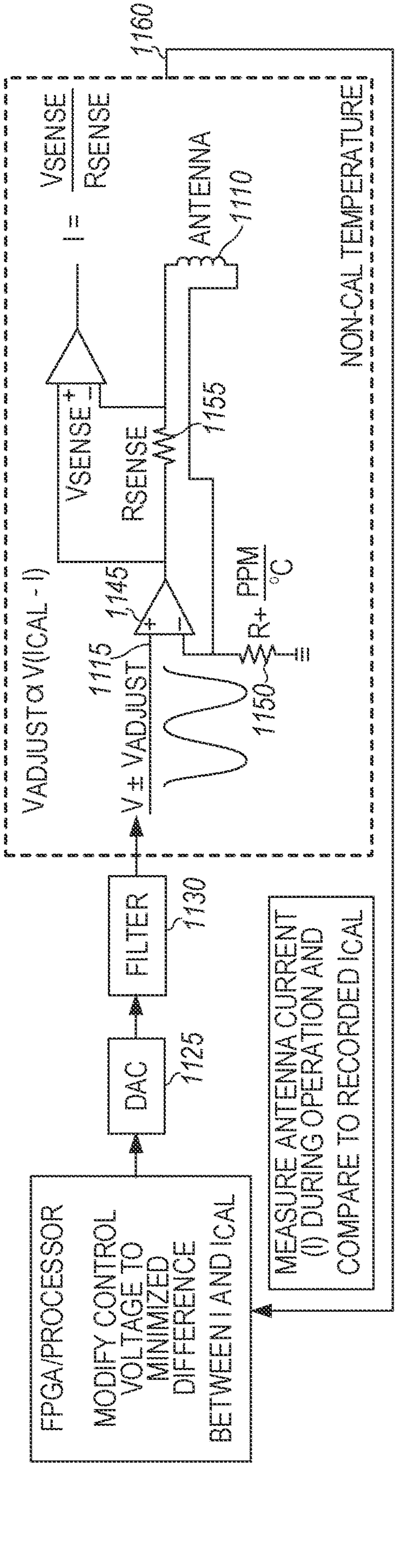
FIG. 11B is a block schematic diagram of a voltage controlled constant current circuit during normal operation according to an example embodiment.

The input voltage amplitude programmed into the DAC 1125 can then be continuously adjusted by the processor or FPGA to minimize the difference between I and $I_{cal}$ during operation as illustrated in FIG. 11B. Therefore, the new control voltage would be $V \pm V_{adjust}$ instead of just V used during the calibration process.

Wireless sensor synchronization is provided in a further embodiment. Normally, in a wired system with synchronous demodulation, synchronization between the transmitter circuits (drivers for the antenna pods) and receive circuits (front end circuitry connected to sensors and/or antenna pods can be accomplished by using a single system control IC (processor or FPGA), or for a system with distributed control, the input clocks can be shared and/or a common synchronization pulse can be used throughout the system.

In a wireless network, neither option is directly possible, which makes synchronous sampling and demodulation more challenging. To compensate for this asynchronous behavior, the waveforms driven or measured from the antenna pods can be modulated with various synchronization waveforms such as a sine wave, triangle wave, etc.

Figure 12:
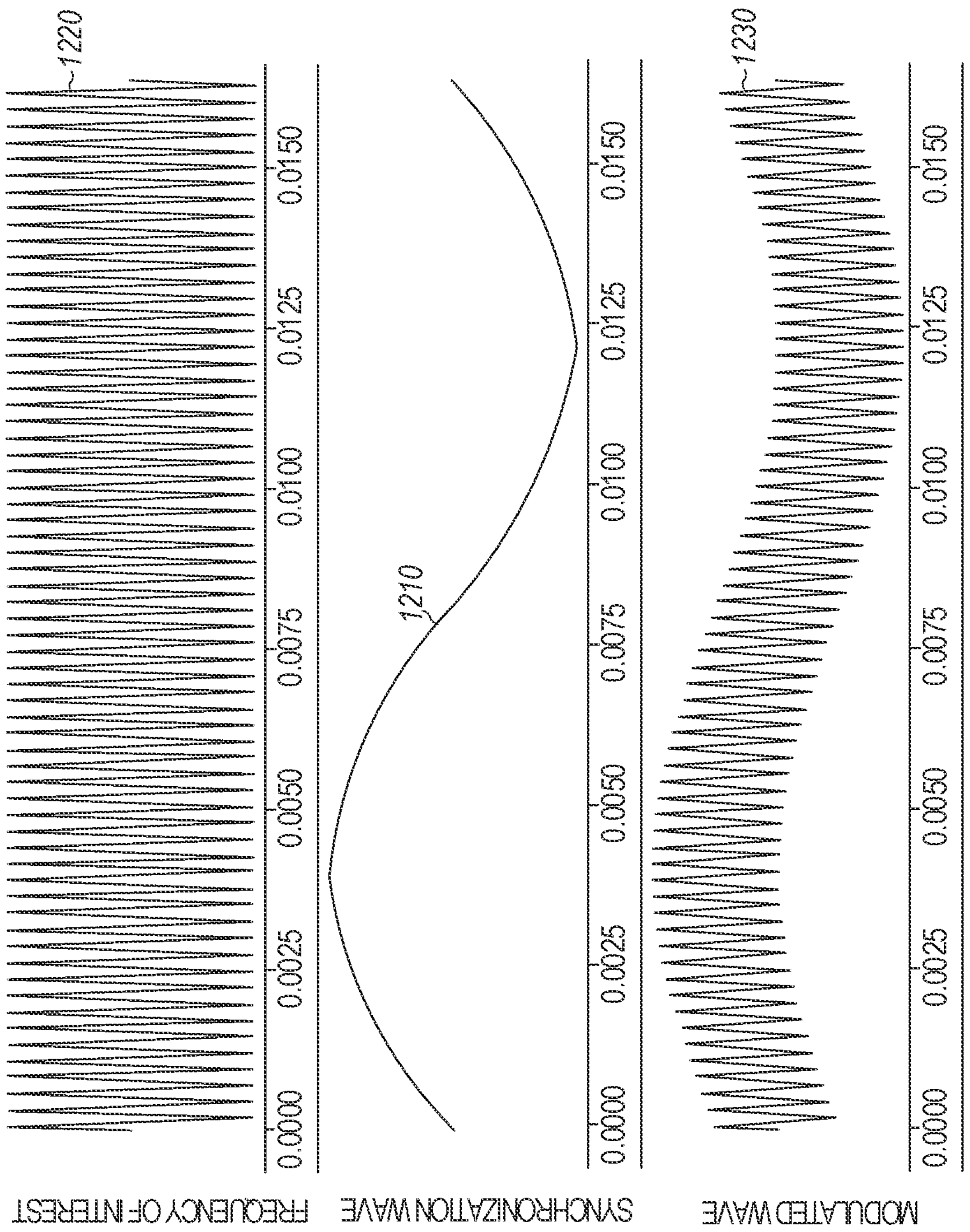
FIGS. 12 and 13 illustrate different synchronization waveforms for wireless sensors according to an example embodiment.
Figure 13:
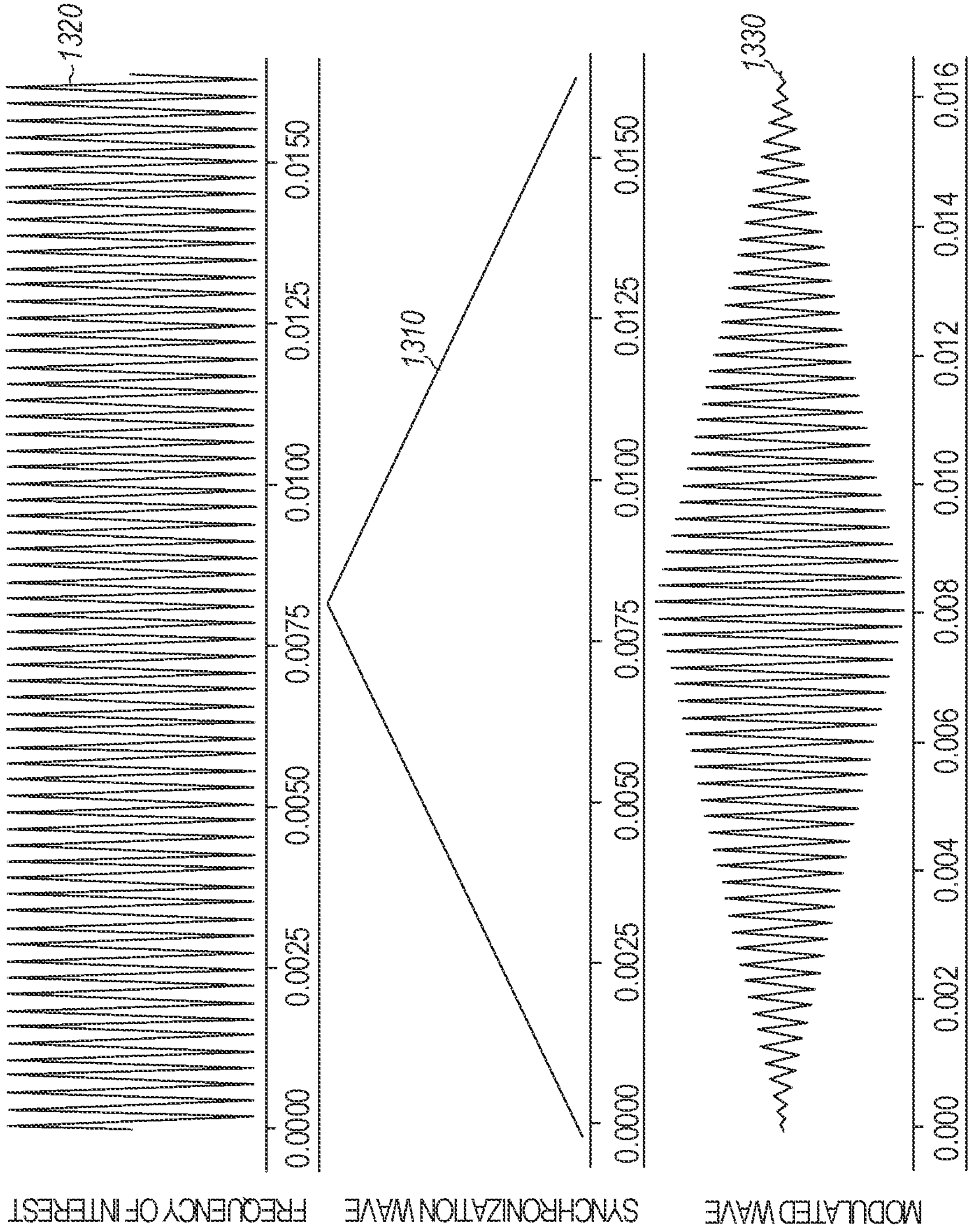

FIGS. 12 and 13 illustrate different synchronization waveforms at 1100 and 1200 respectively. In any given system, the synchronization waveform is often a common factor of all frequencies generated by the system. For example, in a system with three frequencies (1000 Hz, 1100 Hz, and 1200 Hz), the synchronization frequency could be 100 Hz as illustrated by sinusoidal waveform 1210 in FIG. 12 and triangle waveform 1310 in FIG. 13. The frequency is selected because all three frequencies are an integer multiple of 100 Hz and the three frequencies are separated by 100 Hz from one another. The synchronization waveform described above would be periodic and its frequency would match the synchronization frequency (100 Hz in this case)

With this modulation in place (during calibration and/or during normal operation), when each receiver samples data, the synchronization waveform 1210 or 1310 can be used to frame and synchronize the other frequency data through various methods. This modulation could also be enabled periodically to re-synchronize the system depending on the relative clock drift over time.

For example, in FIG. 12, waveform 1220 is the signal of interest, signal 1210 is the synchronization waveform, and waveform 1230 is the combination of the two. Waveform 1210 can be parsed from the received waveform 1230 using a demodulation method. Another option, shown in FIG. 13 may be with a correlation method. The base waveform 1320 is modulated with the triangle waveform 1310 to produce the combined modulated waveform 1330. The waveform 1330 shows a perfectly in phase response, but for most real cases, there will be a non-zero phase shift in the received signal. Correlating the waveform received to the expected "perfect" modulated waveform shows how much the received waveform is actually shifted. This shift can then be taken into account during demodulation to accomplish synchronous demodulation in the wireless system.

Figure 14:
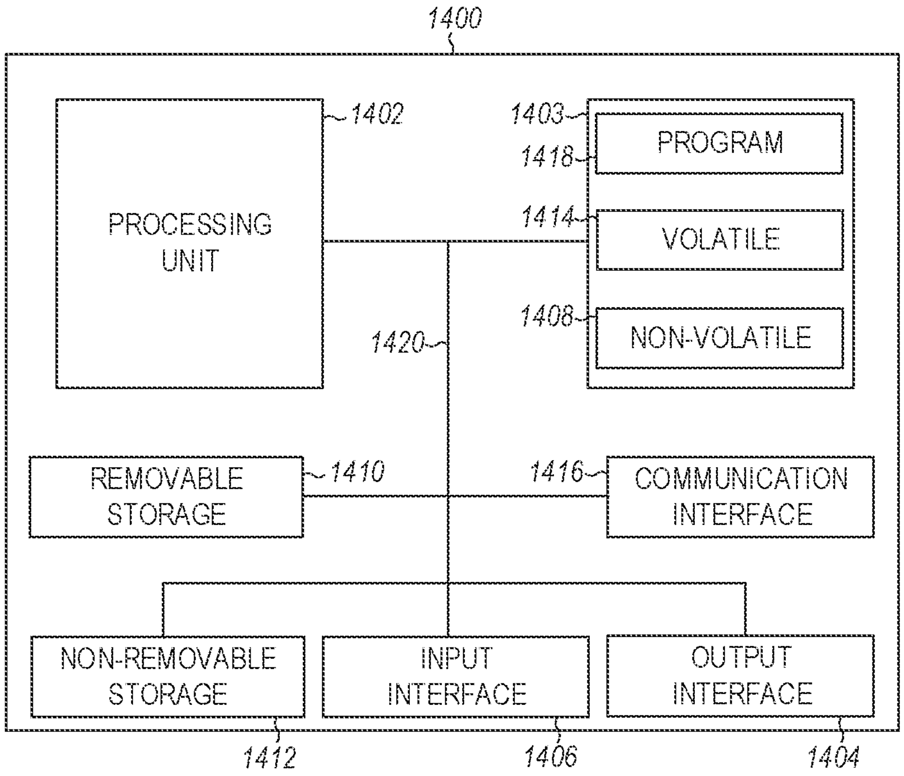
FIG. 14 is a block schematic diagram of a computer system to implement and execute one or more methods, including at least signal processing for driving pods and synchronizing signals according to an example embodiment.

FIG. 14 is a block schematic diagram of a computer system 1400 to implement and execute one or more methods, including at least signal processing for driving pods and synchronizing signals according to example embodiments. All components need not be used in various embodiments, and the system may comprise a field programmable gate array or other circuitry capable of performing methods and algorithms.

One example computing device in the form of a computer 1400 may include a processing unit 1402, memory 1403, removable storage 1410, and non-removable storage 1412. Although the example computing device is illustrated and described as computer 1400, the computing device may be in different forms in different embodiments. For example, the computing device may instead be a smartphone, a tablet, smartwatch, smart storage device (SSD), or other computing device including the same or similar elements as illustrated and described with regard to FIG. 14. Devices, such as smartphones, tablets, and smartwatches, are generally collectively referred to as mobile devices or user equipment.

Although the various data storage elements are illustrated as part of the computer 1400, the storage may also or alternatively include cloud-based storage accessible via a network, such as the Internet or server based storage. Note also that an SSD may include a processor on which the parser may be run, allowing transfer of parsed, filtered data through I/O channels between the SSD and main memory.

Memory 1403 may include volatile memory 1414 and non-volatile memory 1408. Computer 1400 may include—or have access to a computing environment that includes—a variety of computer-readable media, such as volatile memory 1414 and non-volatile memory 1408, removable storage 1410 and non-removable storage 1412. Computer storage includes random access memory (RAM), read only memory (ROM), erasable programmable read-only memory (EPROM) or electrically erasable programmable read-only memory (EEPROM), flash memory or other memory technologies, compact disc read-only memory (CD ROM), Digital Versatile Disks (DVD) or other optical disk storage, magnetic cassettes, magnetic tape, magnetic disk storage or other magnetic storage devices, or any other medium capable of storing computer-readable instructions.

Computer 1400 may include or have access to a computing environment that includes input interface 1406, output interface 1404, and a communication interface 1416. Output interface 1404 may include a display device, such as a touchscreen, that also may serve as an input device. The input interface 1406 may include one or more of a touchscreen, touchpad, mouse, keyboard, camera, one or more device-specific buttons, one or more sensors integrated within or coupled via wired or wireless data connections to the computer 1400, and other input devices. The computer may operate in a networked environment using a communication connection to connect to one or more remote computers, such as database servers. The remote computer may include a personal computer (PC), server, router, network PC, a peer device or other common data flow network switch, or the like. The communication connection may include a Local Area Network (LAN), a Wide Area Network (WAN), cellular, Wi-Fi, Bluetooth, or other networks. According to one embodiment, the various components of computer 1400 are connected with a system bus 1420.

Computer-readable instructions stored on a computer-readable medium are executable by the processing unit 1402 of the computer 1400, such as a program 1418. The program 1418 in some embodiments comprises software to implement one or more methods and algorithms. A hard drive, CD-ROM, and RAM are some examples of articles including a non-transitory computer-readable medium such as a storage device. The terms computer-readable medium and storage device do not include carrier waves to the extent carrier waves are deemed too transitory. Storage can also include networked storage, such as a storage area network (SAN). Computer program 1418 along with the workspace manager 1422 may be used to cause processing unit 1402 to perform one or more methods or algorithms described herein.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

EXAMPLES

Pod/Pad Examples:

1. A device comprising:
   a pod having first spiral conductor supported on a first insulated substrate, the first spiral conductor shaped to form a magnetic field in response to an electric current flowing through the conductor.
2. The device of example 1 and further comprising multiple additional spiral conductor layers supported on insulated substrates, wherein the first and additional insulated substrates are coupled together such that the spiral conductors are connected in series or parallel and together form sufficiently strong magnetic fields and diverse field geometries.
3. The device of any of examples 1-2 and further comprising a plurality of spaced apart pods supported on a pad.
4. The device of example 3 wherein the pad comprises an adhesive on one side of the pad.
5. The device of example 3 and further comprising multiple pads having connectors for coupling to a pod driver.
6. The device of example 5 wherein the pod driver independently drives the pods.
7. The device of example 6 wherein selected pods are coupled in series or in parallel to generate magnetic fields of the same frequency (series or parallel) or different frequencies (parallel).
8. The device of example 5 wherein selected pods are configured as sensors to be localized using other pods or to provide additional interference detection.
9. The device of example 8 wherein the pods, pads, and/or sensors comprises a battery and circuitry to form wireless pods, pads and/or sensors.

Mapping Examples:

1. A method comprising:
   successively exciting individual antennas on two sets of antennas placed in separate fixed positions, wherein the individual antennas on at least one set have a known fixed location with respect to each other;
   successively measuring responses from antennas that are not excited; and
   reconstructing relative locations of the individual antennas based on the measured responses and known fixed locations to define a navigation space between the two sets.
2. The method of example 1 wherein one of the sets comprises a patch configured to be placed on a patient.
3. The method of example 1 wherein one of the sets comprises emitters.
4. The method of example 1 and further comprising sensing the location of an instrument within the defined navigation space.

Field Mapping Devices:

1. A field mapping system comprising:
   a three-dimensional fixed structure;
   a plurality of magnetic sensors coupled to vertices of the structure having known distances between the sensors; and
   circuitry coupled to the sensors to calculate orientations of the sensors and detect changes in an electromagnetic field within the structure due to external magnetic field sources.
2. A method of using the system of example 1 comprising continuously monitoring and compensating for magnetic field distortions within the structure by actuating selected ones of the plurality of magnetic sensors.

Accurate Environmentally Compensated Current Drivers for Antennas:

1. A current driver for an antenna pod, the current driver comprising:
   a power amplifier having an inverting input, a non-inverting input, and an output providing an output current;
   an antenna pod coupled between the output of the power amplifier and the inverting input of the power amplifier to be driven by the output current;
   a voltage source coupled to the non-inverting input of the power amplifier to drive the power amplifier with an input voltage;
   a feedback loop including a current sense coupled to an output of the power amplifier and a sensed voltage used by the voltage source to adjust the input voltage based on the sensed current.
2. The current driver of example 1 wherein the input voltage comprises an alternating current voltage.
3. The current driver of example 1 wherein the current sensor comprises:
   a sense resistor coupled between the output and the antenna pod, and
   an amplifier coupled across the sense resistor.
4. The current driver of example 3 wherein the voltage source comprises a digital controller coupled to receive a digital representation of the sensed current and modify the input voltage to maintain the sensed current at a predetermined value.
5. The current driver of example 4 wherein the predetermined value comprises a calibration current.
6. The current driver of example 4 wherein the voltage source further comprises a digital to analog converter and a filter coupled to provide the input voltage to the power amplifier non-inverting input.

Sensor Synchronization:

1. A method of synchronizing a system of wireless magnetic sensors, the method comprising:
   driving at least one of the magnetic sensors with an alternating current input signal; and
   imposing a synchronization signal on the input signal, wherein the input signal frequency is an integral multiple of the frequency of the synchronization signal.
2. The method of example 1 wherein the input signal comprises two input signals having different frequencies, each of which is an integral multiple of the synchronization frequency.
3. The method of any of examples 1-2 wherein the frequencies are all separated by a single frequency in the range of 10 to 1000 Hz.
4. The method of any of examples 1-3 and further comprising:
   sensing the magnetic field, created by driving at least one antenna pod, by at least one of the magnetic pods or sensors that is not driven; and
   using the synchronization signal in the sensed magnetic field to frame and synchronize signals in the sensed magnetic field.
5. The method of any of examples 1-4 wherein the synchronization signal comprises a sine wave.
6. The method of any of examples 1-4 wherein the synchronization signal comprises a triangle wave.
7. The method of any of examples 1-4 wherein the synchronization signal comprises an arbitrary periodic waveform.

The invention claimed is:

1. A magnetic navigation method comprising:

positioning a set of planar pads in a non-coplanar configuration to define a navigation space, wherein at least one first planar pad of the set of planar pads has at least three antenna elements having coils in fixed, known locations parallel to and supported by the at least one planar pad of the set of planar pads and at least one second planar pad of the set of planar pads having at least one antenna element, each of the at least three antenna elements and the at least one antenna element comprising multiple turns of a conductor, each turn supported on and parallel to one layer of the planar pad it is supported by;

exciting individual ones of the at least three antenna elements on the at least one first planar pad of the set of planar pads to generate magnetic fields;

measuring the generated magnetic fields at the at least one antenna element on the at least one second planar pad of the set of planar pads;

determining a location and orientation of the at least one antenna element on the at least one second planar pad of the set of planar pads based on the measured magnetic fields and the fixed, known locations and orientations of the at least three antenna elements on the at least one first planar pad of the set of planar pads; and following determining the location and orientation of the at least one antenna element on the at least one second planar pad of the set of planar pads, performing one of:
   (i) transmitting magnetic signals from at least three antenna elements of the set of planar pads and receiving the transmitted magnetic signals at a device within the navigation space; or
   (ii) transmitting magnetic signals from a device within the navigation space and receiving the transmitted magnetic signals at at least three antenna elements of the set of planar pads; and determining a location and orientation of the device based on the transmitted magnetic signals received at the device according to (i) or received at the at least three antenna elements of the set of planar pads according to (ii).

2. The method of claim 1 wherein the device comprises multiple antenna elements spaced apart and supported on a first pad.

3. The method of claim 2 and further comprising attaching the device to an object within or around the navigation space.

4. The method of claim 2 and wherein the at least one antenna element on the at least one second planar pad includes antenna elements, and further comprising configuring the antenna elements on the at least one second planar pad to receive magnetic signals transmitted from the device within the navigation space.

5. The method of claim 4 wherein the set of planar pads are supported by a three dimensional rigid structure having planes that intersect to form vertices having known distances.

6. The method of claim 5 and further comprising detecting changes in the magnetic fields which are indicative of interference.

7. The method of claim 1 wherein the transmitting magnetic signals from the set of planar pads comprises individually driving the at least three antenna elements on the at least one first planar pad of the set of planar pads.

8. The method of claim 7 wherein one or more antenna drivers continuously monitor and adjust magnitudes of currents driven through the at least three of the antenna elements on the at least one first planar pad of the set of planar pads.

9. The method of claim 7 wherein the at least three antenna elements from the at least one first planar pad are coupled in series or in parallel and wherein the method further comprises driving the at least three antenna elements from the at least one first planar pad to generate magnetic fields with distinct geometries.

10. The method of claim 7 and further comprising driving the at least three antenna elements on the at least one first planar pad of the set of planar pads to generate magnetic fields with distinct geometries.

11. A magnetic navigation method comprising:

positioning a first pad in a first fixed position, the first pad having at least three first antenna elements having coils in fixed, known locations parallel to and supported by a first planar surface of the first pad;

configuring a moveable second pad in a second position, the second pad having at least one second antenna element having coils parallel to and supported by a second planar surface of the second pad and not coplanar with the first antenna elements;

exciting the first antenna elements to generate first magnetic fields or the at least one second antenna element to generate a second antenna element magnetic field;

measuring the generated first magnetic fields at the at least one second antenna element, or the generated second antenna element magnetic field at the first antenna elements;

identifying a location and orientation for the at least one second antenna element based on the fixed known locations and orientations of the first antenna elements by processing the measured first magnetic fields measured at the at least one second antenna element or the measured second antenna element magnetic field measured at the first antenna elements using an iterative Levenberg-Marquardt minimization, triangulation, or trilateration routine, wherein the first pad and the second pad define a configured navigation space;

following the identifying of the location and orientation for the at least one second antenna element, performing one of:

(i) transmitting magnetic signals from the at least three antenna elements and receiving the transmitted magnetic signals at a device within the configured navigation space; or (ii) transmitting magnetic signals from a device within the configured navigation space and receiving the transmitted magnetic signals at the at least three first antenna elements;

and determining a location and orientation of the device based on the transmitted magnetic signals received at the device according to (i) or received at the at least three first antenna elements according to (ii).

* * * * *